(12) United States Patent
Chua

(10) Patent No.: US 9,050,085 B2
(45) Date of Patent: Jun. 9, 2015

(54) MEDICAL LENS ASSEMBLIES AND STERILE DRAPES WITH A LENS ASSEMBLY

(71) Applicant: Medline Industries, Inc., Mundelein, IL (US)

(72) Inventor: Mark Spencer G. Chua, Glenview, IL (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 14/489,752

(22) Filed: Sep. 18, 2014

(65) Prior Publication Data

US 2015/0002937 A1    Jan. 1, 2015

Related U.S. Application Data

(62) Division of application No. 14/163,630, filed on Jan. 24, 2014, now Pat. No. 8,864,320, which is a division of application No. 13/941,725, filed on Jul. 15, 2013, now Pat. No. 8,672,489, which is a division of application No. 12/649,127, filed on Dec. 29, 2009, now Pat. No. 8,506,094.

(51) Int. Cl.
*A61B 19/08*    (2006.01)
*G02B 21/00*    (2006.01)
*A61B 19/00*    (2006.01)
(Continued)

(52) U.S. Cl.
CPC .......... *A61B 19/081* (2013.01); *G02B 21/0012* (2013.01); *A61B 19/5223* (2013.01); *Y10T 29/49826* (2015.01); *G02B 27/0006* (2013.01); *G02B 23/16* (2013.01); *A61B 19/5212* (2013.01); *Y10S 359/90* (2013.01)

(58) Field of Classification Search
CPC ............. A61B 19/081; A61B 19/5212; A61B 19/5223; G02B 21/0012; G02B 23/16; G02B 27/0006
USPC ............................ 359/510, 511, 900; 128/849
See application file for complete search history.

(56) References Cited

U.S. PATENT DOCUMENTS 1,283,963 A    11/1918  Takahashi
2,889,629 A     6/1959  Darkenwald
(Continued)

OTHER PUBLICATIONS

International Search Report, mailed Sep. 8, 2011, which issued in corresponding International Patent Application No. PCT/US2010/060998 (5 pages).

(Continued)

*Primary Examiner* — Ricky D Shafer
(74) *Attorney, Agent, or Firm* — Nixon Peabody LLP

(57) ABSTRACT

Medical lens assemblies and sterile drapes with a lens assembly are presented herein. In one embodiment, a lens assembly includes an annular lens housing that is attachable to a medical drape. The lens housing is configured to releasably attach to a medical device, such as a surgical microscope. An annular lens cover holder is removably attachable to the lens housing. A lens cover for shielding the objective lens is pivotably hinged to the lens cover holder. In another embodiment, a drape assembly includes a flexible body sized to cover an optical device. A lens housing attached to the drape body is engageable with the optical device to attach proximate an objective lens thereof. A lens cover holder is removably attached to the lens housing to rotate about a first axis. A lens cover is mounted to the lens cover holder to pivot about a second, different axis.

20 Claims, 2 Drawing Sheets

(51) Int. Cl.
   *G02B 27/00*   (2006.01)
   *G02B 23/16*   (2006.01)

(56) References Cited

U.S. PATENT DOCUMENTS

| | | | |
|---|---|---|---|
| 3,796,477 A | 3/1974 | Geraci | |
| 3,942,864 A | 3/1976 | Numbers | |
| 4,266,663 A | 5/1981 | Geraci | |
| 4,385,812 A | 5/1983 | Wille et al. | |
| 4,561,540 A | 12/1985 | Hunter et al. | |
| 4,564,270 A | 1/1986 | Willie | |
| 4,799,779 A | 1/1989 | Mesmer | |
| 4,909,617 A | 3/1990 | Boyd | |
| 5,155,624 A | 10/1992 | Flagler | |
| 5,311,358 A * | 5/1994 | Pederson et al. | 359/510 |
| 5,467,223 A * | 11/1995 | Cleveland et al. | 359/510 |
| 5,608,574 A | 3/1997 | Heinrich | |
| 5,682,264 A | 10/1997 | Cleveland et al. | |
| 5,853,363 A | 12/1998 | Vought | |
| 6,024,454 A * | 2/2000 | Horan et al. | 359/510 |
| 6,116,741 A | 9/2000 | Paschal | |
| 6,257,730 B1 | 7/2001 | Kleinberg et al. | |
| 6,283,125 B1 | 9/2001 | McNeirney et al. | |
| 6,416,189 B1 | 7/2002 | Watson et al. | |
| 6,876,503 B1 | 4/2005 | Weaver et al. | |
| 7,232,230 B2 | 6/2007 | Bala | |
| 7,234,824 B2 | 6/2007 | Langley | |
| 7,374,295 B2 | 5/2008 | Fuchs et al. | |
| 8,506,094 B2 * | 8/2013 | Chua | 359/510 |
| 8,672,489 B2 * | 3/2014 | Chua | 359/510 |
| 8,864,320 B2 * | 10/2014 | Chua | 359/510 |
| 2005/0088763 A1 | 4/2005 | Weaver et al. | |
| 2005/0094269 A1 * | 5/2005 | Moses et al. | 359/510 |
| 2006/0139753 A1 | 6/2006 | Moses et al. | |
| 2007/0064309 A1 | 3/2007 | Luloh et al. | |
| 2008/0144178 A1 * | 6/2008 | Dillon et al. | 359/510 |

OTHER PUBLICATIONS

International Written Opinion, mailed Sep. 8, 2011, which issued in corresponding International Patent Application No. PCT/US2012/060998 (4 pages).

* cited by examiner

MEDICAL LENS ASSEMBLIES AND STERILE DRAPES WITH A LENS ASSEMBLY

CLAIM OF PRIORITY AND CROSS-REFERENCE TO RELATED APPLICATIONS

This application is a divisional of U.S. patent application Ser. No. 14/163,630, filed on Jan. 24, 2014, now allowed, which is a divisional of U.S. patent application Ser. No. 13/941,725, filed on Jul. 15, 2013, now U.S. Pat. No. 8,672,489 B2, which is a divisional of U.S. patent application Ser. No. 12/649,127, which was filed on Dec. 29, 2009, now U.S. Pat. No. 8,506,094 B2all of which are incorporated herein by reference in their respective entireties.

TECHNICAL FIELD

The present disclosure relates generally to optical devices requiring a sterile field. More particularly, the present disclosure relates to medical lens assemblies and sterile drapes with one or more lens assemblies for maintaining a sterile field.

BACKGROUND

During a surgical operation, the surgical site and surrounding areas must remain sterile. A "surgical field" is an environmentally-controlled area in a typical hospital operating room where the risk of infection, such as from naturally occurring organisms (e.g., bacteria), is minimized or eliminated. The sterility of the surgical field is typically controlled by limiting the introduction of infection-causing bacteria and other contaminants. In general, this is achieved by implementing strict regulations over the personnel and equipment present in the operating room.

Surgical drapes are often utilized during surgery in the operating room to minimize the risk of infection to surgical patients and to protect medical equipment from the surgical field. An array of different surgical drapes may be placed over the patient and the medical equipment to create a sterile barrier, preventing microorganisms and other contaminants that may cause infections from migrating to and from exposed tissue, bodily fluids, etc. For example, bodily fluids secreted during surgery that would otherwise settle on medical equipment, which would then become contaminated and potentially hazardous, will instead ultimately settle on the drapes and not on the draped medical equipment.

Optical devices, such as surgical microscopes and cameras, have become an integral part of many operating rooms. Microscopes used for surgery are generally permanent fixtures of the operating room, typically mounted to the ceiling or a wall, or supported on a floor-mounted stand. Surgical microscopes often have an articulated cantilever support arrangement to facilitate movement of the microscope over an operating zone. Surgical microscopes normally take on very complex shapes, often having several sets of eyepieces that permit the surgeon and others to simultaneously view the magnified area under the microscope's objective lens. In addition to the ocular segments, one or more viewing tubes and/or laser arms (depending on design) project out from the microscope housing.

Due to its complex geometry, it is very time consuming and difficult to thoroughly sterilize an entire microscope assembly before and after each surgical procedure. As such, it is common practice to cover the microscope with a disposable surgical drape. The drape typically comprises a flexible sheet-form material that covers all of the components of the surgical microscope, including the ocular ports, the viewing tubes, the microscope head, and the structure that supports the head. The disposable surgical drape is typically manufactured and packaged under sterile conditions so that, when unpackaged and placed on a microscope, the drape creates a sterile field around the microscope and its components.

The microscope drape is often initially affixed to the microscope at the lens housing for the objective lens, to orient the drape with respect to other structure of the microscope. For example, some microscope drapes include an annular positioning sleeve that is attached to or integral with an elongated tubular cover. The positioning sleeve fits onto the objective lens housing of the microscope to initially affix the sterile drape to the microscope assembly. Once the surgical drape is attached to the objective lens housing, the remaining portions of the drape can be conveniently unfolded and positioned to cover the remainder of the microscope assembly.

In order to protect the objective lens without obstructing the view of the surgical area, a transparent protective lens (also referred to in the art as "lens cover") adapted to shield the objective lens is usually associated with the drape assembly. For example, in some prior art configurations, a housing comprising a rigid mounting ring, which encloses a transparent-plastic lens, is integrally-formed with the drape. The mounting ring housing is adapted to attach, typically via a separate adaptor or clamp, to the outer diameter of the microscope objective lens housing. Some designs incorporate an interchangeable lens cover that can be removed from the lens cover housing and replaced with a substitute lens cover.

Unlike typical microscopes, the illuminating light source of many surgical microscopes comes from above and shines onto the lens cover covering the objective lens, which may generate glare when the surgeon looks through the microscope. Moreover, during surgical operations, the lens cover can be splattered by fluids from the surgery, such as blood, which will obscure the surgeon's vision. To rectify this problem, someone on the surgical team is conventionally required to either wipe the lens cover (which can further obscure the vision), remove and replace the lens cover (which requires a lens cover be taken from another drape assembly), or replace the entire drape (which temporarily breaks the sterile field, is time consuming, and wastes another entire drape assembly). Finally, different surgical microscopes use different size objective lenses. Thus, a facility with a variety of different surgical microscopes is required to carry an array of different surgical drape assemblies with lens housings and lens covers of various sizes, increasing overhead costs and unnecessarily complicating the preparation process for the operating room.

BRIEF DESCRIPTION OF THE DRAWINGS

Various advantages of the invention will become apparent upon reading the following detailed description and upon reference to the drawings.

Figure 1:
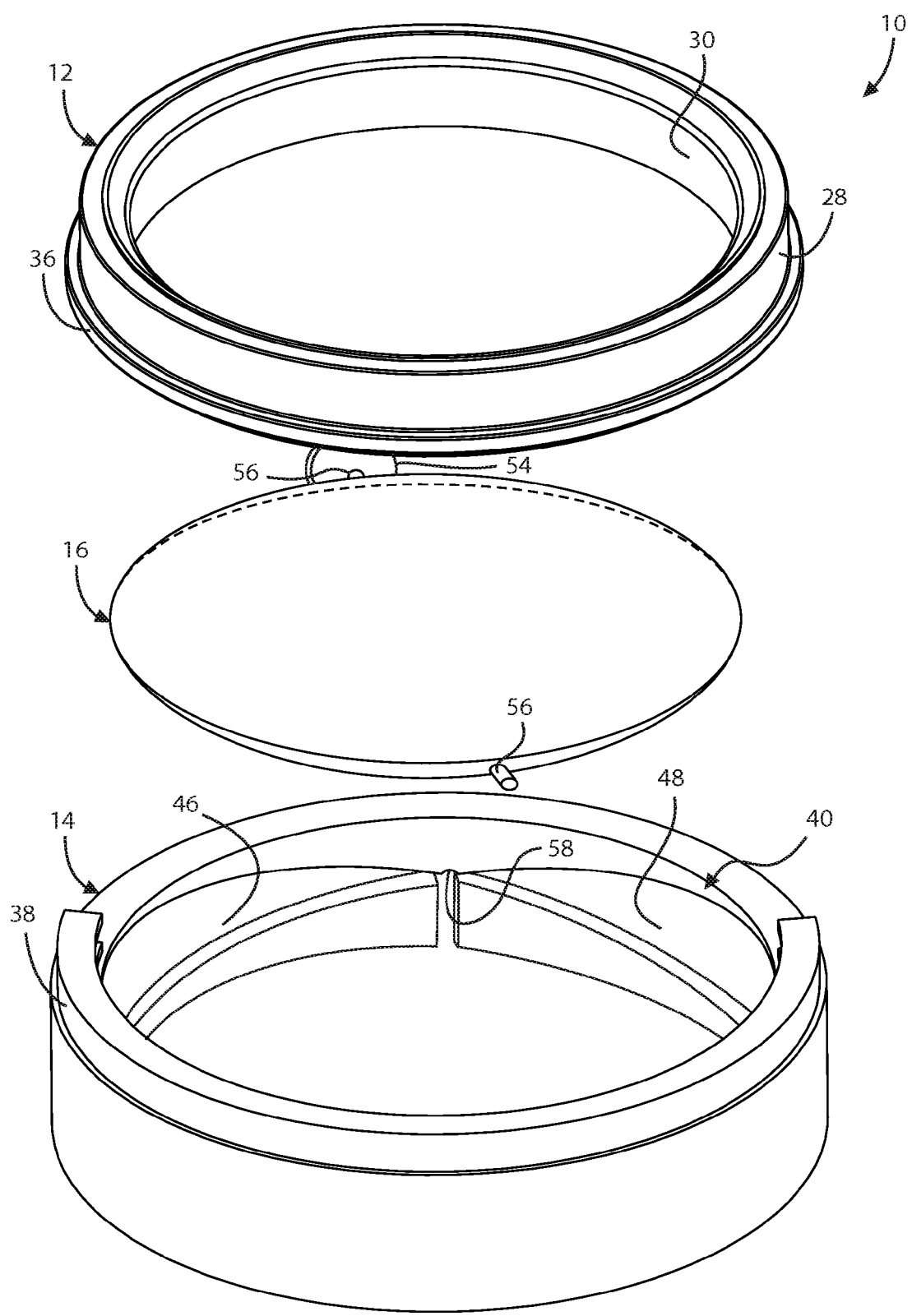
FIG. 1 is an exploded perspective-view illustration of a protective lens assembly in accordance with one embodiment of the present invention.

While the invention is susceptible to various modifications and alternative forms, specific embodiments are shown by way of example in the drawings and will be described in detail herein. It should be understood, however, that the invention is not intended to be limited to the particular forms disclosed.

Rather, the invention is to cover all modifications, equivalents, and alternatives falling within the spirit and scope of the invention.

DESCRIPTION OF ILLUSTRATIVE EMBODIMENTS

While this invention is susceptible of embodiment in many different forms, there is shown in the drawings and will herein be described in detail representative embodiments of the invention with the understanding that the present disclosure is to be considered as an exemplification of the principles of the invention and is not intended to limit the broad aspect of the invention to the embodiments illustrated. To that extent, elements and limitations that are disclosed, for example, in the Drawings, Abstract, and Description of the Illustrative Embodiments section, but not explicitly set forth in the claims, should not be incorporated into the claims, singly or collectively, by implication, inference or otherwise.

The present invention will be described herein in the context of a surgical lens assembly and a sterile surgical drape assembly for covering a surgical microscope and creating a barrier between a sterile field of an operating room and a surgical microscope. However, the present invention is by no means limited to this particular application. By way of non-limiting example, the concepts of the present invention may just as easily be incorporated into sterile drape assemblies used in any procedure requiring a sterile field, including surgical procedures, non-surgical medical procedures, and non-medical operations (e.g., in a scientific research clean room). Moreover, the lens assemblies and drape assemblies of the present invention may be used on surgical microscopes and various other optical devices, such as medical imaging equipment (e.g., surgical cameras), operating room light fixtures, etc., without departing from the intended scope and spirit of the present invention. Finally, the drawings presented herein are not to scale and are provided purely for instructional purposes. As such, absent explicit claim language to the contrary, the individual and relative dimensions and orientations shown in the drawings are not to be considered limiting.

Referring to the drawings, wherein like reference numerals refer to like components throughout the several views, FIG. 1 provides an exploded perspective-view illustration of an exemplary medical lens assembly, designated generally as 10, in accordance with various aspects of the present invention. The medical lens assembly 10 includes three primary components: an annular lens housing 12, an annular lens cover holder 14, and a transparent, disc-shaped lens cover 16. Although depicted in FIG. 1 as circular, donut-shaped (i.e., toroidal) components, the lens housing 12 and lens cover holder 14 may take on additional shapes (e.g., elliptical, polygonal, etc.), individually or collectively, depending on the intended application and design requirements of the lens assembly 10. Likewise, the lens cover 16 may take on additional geometric configurations without departing from the scope and spirit of the present invention.

Figure 2:
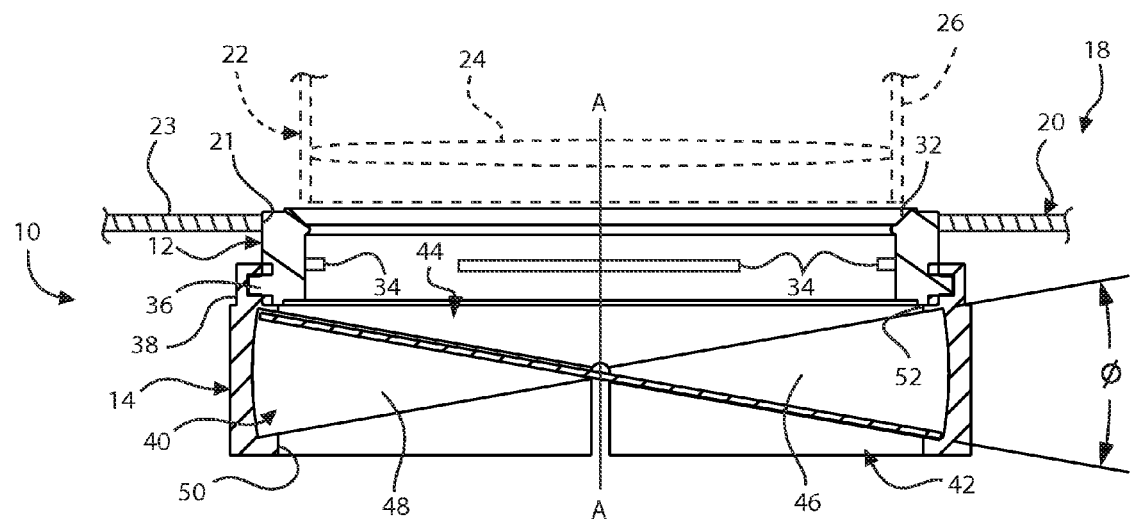
FIG. 2 is a cross-sectional side-view illustration of a sterile drape assembly in accordance one embodiment of the present invention.

The lens housing 12 is attached or attachable to a surgical drape 20 to form a drape assembly 18, as seen in FIG. 2. By way of example, the lens housing 12 may be received in a complementary aperture 21 that is formed through a portion of the drape body 23. An adhesive may then be applied to the outer periphery of the lens housing 12 along the interface between the drape 20 and the lens housing 12, whereby the lens housing 12, and thus the entire lens assembly 10 of FIG. 2, is coupled to the drape 20. Alternatively, the lens housing 12 may be mechanically fastened to (e.g., via fasteners) or integrally formed with the drape body 23.

According to one intended application, the drape assembly 18 of FIG. 2 may be employed, as explained above, to create a physical barrier between a sterile field of an operating room and medical device, represented herein as a surgical microscope (shown hidden at 22 in FIG. 2). In general, the microscope 22 includes an objective lens 24 that is circumscribed by, and generally encased within a cylindrical objective lens housing 26. The microscope 22 includes many other conventional components, such as a microscope body or main housing, one or more eyepieces, a light source, etc. that are well known in the art. Since these components are well known in the art, and are per se not part of the subject invention, these structures will not be discussed or illustrated in detail herein.

The lens housing 12 is configured to engage with and thereby attach to the medical device 22. In the illustrated embodiment, for example, the annular lens housing 12 comprises an outer backing ring, designated as 28 in FIG. 1, with an inner-diameter surface 30 comprised of a flexible material. According to one potential configuration, the outer ring 28 is fabricated from a rigid polymer, such as polypropylene, with an overmolded, soft thermoplastic-elastomer (TPE) forming the inner-diameter surface 30. Alternatively, other materials can be used, such as polyethylene, ABS, or any thermal plastic. The lens housing 12 may be axially pressed or fed onto the outer surface of the objective lens housing 26 of the surgical microscope 22. When circumscribing the objective lens 24, the inner-diameter surface 30 of the lens housing 12 compresses against and frictionally engages the outer-diameter surface of the objective lens housing 26, thereby attaching the drape assembly 18, including the lens assembly 10 and drape body 23, to the surgical microscope 22.

In the embodiment illustrated in FIG. 2, the lens housing 12 is provided with a ramped surface 32 that extends continuously around a forward inner-edge thereof. The ramped surface 32 acts as an angled alignment feature which facilitates engagement between the lens housing 12 and microscope 22 by properly orienting and axially aligning the lens housing 12 with the objective lens housing 26 when being pressed together. The lens assembly 10 may be removed from the microscope 22 by pulling on or otherwise disengaging the lens housing 12 from the objective lens housing 26. It is also envisioned that the lens assembly 10, namely lens housing 12, be operatively coupled to the microscope 22 by alternative means (e.g., via complementary helical threads, snap-fasteners, latches, adaptors, combinations thereof, etc.).

With continuing reference to FIG. 2, the inner-diameter surface 30 of the annular lens housing 12 may include an optional plurality of compliant protrusions 34 that project radially inwardly therefrom. When the lens housing 12 is pressed onto the objective lens housing 26, the compliant protrusions 34 compress or squeeze between the inner-diameter surface 30 of the lens housing 12 and the outer-diameter surface of the objective lens housing 26, thereby increasing the frictional force between the lens housing 12 and objective lens housing 26. Three protrusions 34 are illustrated in FIG. 2; however, more or fewer than three protrusions 34 may be incorporated into the lens housing 12 design. This embodiment allows the inner-diameter surface 30 and the outer backing ring 28 to be molded and formed from the same material.

The surgical drape 20 is preferably made of materials now known or hereinafter developed that are commonly used in medical drapes. Such materials may include, but are not limited to, coated papers and pretreated and/or pre-impregnated cloths, including non-woven and woven fabrics, such as spunbond polypropylene (PPSB), spunlace, spunbond meltblown spunbond (SMS), and combinations thereof. The drape material may also comprise bi-component non-woven materials, tri-laminates, bi-laminates, combinations thereof, and/or any variation of such fabrics. The material may include hydro-entangled materials and other fluid-resistant materials. However, one preferred material for the surgical drape 20 is a clear plastic, such as polyethylene or polyurethane, as the transparency eases application to the surgical microscope 22. It is also possible for the plastic to be of a darker shade, while still being transparent, in order to reduce glare from the drape itself. An "eco drape" type material is also envisioned for the surgical drape 20, such as unbleached drape materials and/or fluorocarbon free drape materials that are biodegradable and/or compostable.

The size and shape of the drape body 23 is sufficient to cover at least a portion, but preferably all of the surgical microscope 22. The geometry and dimensions of the drape 20 may be varied depending upon factors such as the size and design of the microscope 22 and other practical considerations. It is generally desirable that the drape 20 be provided with the appropriate extensions and necessary openings that cover and/or allow access to the various microscope oculars. The drape 20 may also include optional strips of cloth or plastic (not shown), which allow the drape body 23 to be tightened and secured to the microscope 22. For instance, plastic straps may be adhered or otherwise fixed at one end to an outer-side surface of the drape body 23, and provided with adhesive on the opposite end such that the user can wrap the straps around loose drape material, then secure the loose drape material to the microscope 22.

Referencing both FIGS. 1 and 2, the medical lens assembly 10 includes a disposable and/or interchangeable lens cover holder 14, wherein the lens cover holder 14 is easily attachable to and, in some embodiments, detachable from the lens housing 12. According to one exemplary configuration, the lens housing 12 includes a circular flange 36 that protrudes radially outwardly from a bottom edge of the lens housing 12. In the illustrated embodiment, the flange 36 extends continuously around the outer perimeter of the annular lens housing 12. Alternatively, the circular flange 36 may be broken down into a plurality of individual segments, each of which projects radially outwardly from the lens housing 12.

Figure 3:
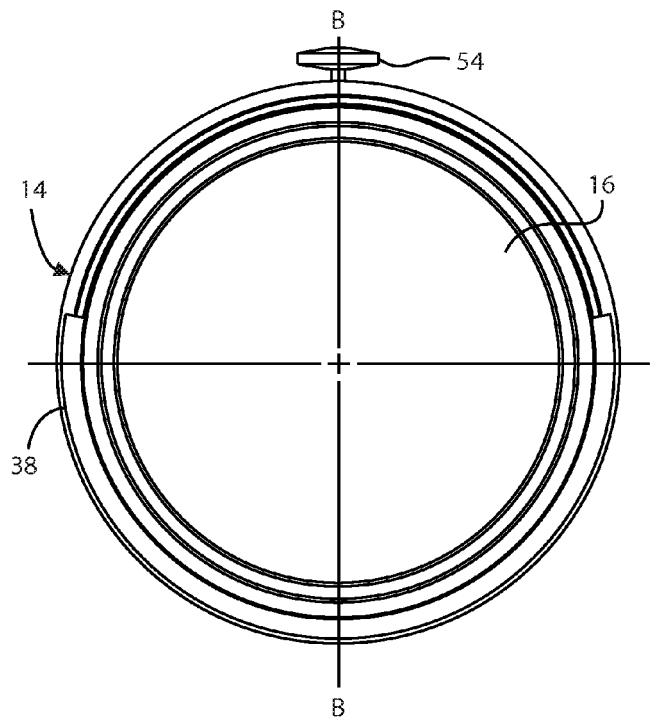
FIG. 3 is a plan-view illustration of a lens cover holder in accordance with one embodiment of the present invention.

Continuing with the above example, the lens cover holder 14 includes a complementary arcuate slot 38 that is configured to receive and mate with the flange 36, thereby attaching the lens cover holder 14 to the lens housing 12. According to the embodiment illustrated in FIG. 1, for example, the complementary arcuate slot 38 is a C-shaped channel that projects from the top surface of the lens cover holder 14. In this example, the arcuate slot 38 extends over approximately 180 degrees about the upper surface of the annular lens cover holder 14, as best seen in FIG. 3. In one preferred configuration, the arcuate slot 38 extends over approximately 200 degrees, with a diameter of at least about 68 mm. To provide a more secure connection and eliminate inadvertent play between the lens housing 12 and the lens cover holder 14, the inner diameter of the arcuate slot 38 is preferably the same as, or just larger than, the outer diameter of the flange 36, as seen in FIG. 2. Recognizably, in an alternate arrangement, the circular flange 36 may project from the lens cover holder 14, whereas the complementary arcuate slot 38 would be disposed on an appropriate surface of the lens housing 12. In yet another alternate arrangement, it is also possible that the lens housing 12 and the lens cover holder 14 be fabricated as an inseparable, single-piece unitary structure.

In order to attach the lens cover holder 14 to the lens housing 12 (and, thus, the drape assembly 18 in the embodiment of FIG. 2), the lens housing 12 and/or lens cover holder 14 are shifted or slid towards one another along a mutual lateral-plane—e.g., in a shearing-type motion. The flange 36 is pressed into the arcuate slot 38 until the lens housing 12 and the lens cover holder 14 (and, thus, the flange 36 and slot 38) are generally concentric. Due to the length of the circular arc of the arcuate slot 38, the arcuate slot 38 acts to cup and retain the flange 36 therein. The flange 36 and/or slot 38 may be fabricated from a flexible material to facilitate the flange 36 being press-fit into engagement with the arcuate slot 38.

The lens cover holder 14 is selectively rotatable with respect to the lens housing 12 when operatively engaged therewith. That is, when the flange 36 is properly positioned inside the arcuate slot 38, the entire lens cover holder 14, including the lens cover 16, can be selectively rotated about a first axis A (FIG. 2) in both the clockwise and counterclockwise direction without having to disengage the lens cover holder 14 from the lens housing 12 and/or the drape body 23. As explained below, the selective rotation of the lens cover holder 14 is in addition to, and independent of, the selective pivoting of the lens cover 16.

According to one advantageous facet of the present invention, the lens housing 12 can be designed as a universal interface for attaching a standard-sized lens cover holder 14 to any of an array of different microscopes with objective lenses of varying sizes. For instance, multiple versions of the lens housing 12 can be designed with an attachment flange 36 that has a common, predetermined outer circumference to mate with a standardized complementary arcuate slot 38 of a predetermined diameter and geometric configuration. The inner circumference of the lens housing 12, however, can be adjusted to accommodate (e.g., press-fit onto and frictionally engage) different-sized objective lens housings.

A universal lens cover holder 14 and lens cover 16, as taught herein, allows the end user to have a universal store of lens cover holders separate from a stock of surgical microscope drape assemblies. This feature helps reduce overhead costs by eliminating the need to stockpile a variety of different replacement drape assemblies and/or replacement lens cover holders. This system also eliminates the need for a separate permanent or semi-permanent adaptor attached to the objective lens.

Referring to FIGS. 2 and 3, the lens cover holder 14 secures the lens cover 16 at an angled position, shielding the objective lens 24 and separating the microscope 22 from the sterile field. By way of example, the lens cover 16 is mounted, hinged or otherwise attached to the lens cover holder 14 such that the lens cover 16 can be selectively pivoted with respect to the lens cover holder 14. As seen with reference to the embodiment illustrated in FIG. 2, the lens cover holder 14 includes an internal chamber, designated generally at 40 in FIG. 2, within which the lens cover 16 is hingedly attached—e.g., via integrally-formed pivot arms 56 received in complementary holes 58 formed in the lens cover holder 14 (only one of which as visible in FIG. 1, but a second hole being formed on an opposing side of the lens cover holder 14 to the one shown). Alternatively, the lens cover 16 may be mounted on hinges that are integrally-formed with the lens cover holder 14. The lens cover 16 spans transversely across the internal chamber 40 of the lens cover holder 14, effectively blocking the path between longitudinally offset openings 42 and 44 of the lens cover holder 14.

The lens cover 16 pivots about a second axis B that is different from the first axis about which the lens cover holder 14 rotates, as seen with comparative reference to FIGS. 2 and 3. In one particular facet, the second axis B is generally orthogonal with respect to the first axis A. The lens cover pivot axis B, for example, may be oriented generally transversely with respect to the longitudinal axis of the annular lens cover holder 14; the lens cover holder axis of rotation A being coaxially aligned with the longitudinal axis of the lens cover holder 14. Likewise, as seen in FIG. 2, the first axis A may be generally coaxially oriented with respect to the viewing axis (i.e., the longitudinal axis) of the objective lens 24, whereas the second axis B may be generally transverse with respect to the viewing axis of the objective lens 24. The angular and planar offset between the lens cover housing 14 axis of rotation A and the lens cover 16 axis of pivot B may be varied depending upon such factors as the intended application, design requirements, and other practical concerns relating the lens assembly 10 and drape assembly 18. To that end, the lens cover 16 pivot angle ø, FIG. 2, which is preferably at least about 20 degrees, may be modified as required. An optional tilt knob 54 may be operatively attached to or integrally formed with the lens cover 16, providing the user a mechanical interface for selectively pivoting the lens cover 16.

The internal chamber 40 illustrated in FIGS. 1 and 2 is a butterfly chamber, with first and second semi-circular, wedge-shaped sections 46 and 48, respectively. In other words, each section 46, 48 is shown in FIGS. 1 and 2 as an approximately 20° truncated-segment of a sphere with a radius that is generally coextensive with the radius of the lens cover 16. The first wedge-shaped section 46 nests a first-half of the circular lens cover 18, whereas the second wedge-shaped section 48 nests a second-half of the circular lens cover 18. The internal chamber 40 of the lens cover holder 14 also includes first and second angularly offset shoulders 50 and 52, respectively. The shoulders 50, 52 cooperate to limit the range of pivoting of the lens cover 16 by obstructing the rotational path of the lens cover 16. By way of clarification, when the lens cover 16 reaches a predetermined angular threshold (e.g., 20° in FIG. 2), each shoulder 50, 52 will press against a respective opposing portion of the lens cover 16, restricting the lens cover 16 from transitioning any further.

In the embodiment shown, the lens cover 16 is shown as a thin, flat, circular lens that is fabricated from a transparent or generally-transparent material, such as polycarbonate. The lens cover 16 may be coated or laminated with anti-glare or anti-fog materials. The lens cover holder 14, on the other hand, is a generally-rigid, opaque material, such as polypropylene, that may colored black or other comparable pigments. The pivotable lens cover 16 described hereinabove deflects unwanted glare away from the ocular path and allows the end user to re-direct the glare to whatever direction he/she desires. In embodiments where the lens cover 16 is not curved, distortion of the original microscope vision is further minimized. Also, by coloring the lens cover housing (e.g., black), the amount of light being reflected back to the lens cover 16 is minimized.

The medical lens assembly 10 described hereinabove allows for the replacement of only the removable lens cover holder 14 when the lens cover 16 is obscured by fluids. This eliminates requiring the user to waste an entire, new drape assembly to find a replacement for the lens cover. This particular facet of the present invention also eliminates the necessity of having to operate without a lens cover or having to wipe the lens cover, thus potentially obscuring visual clarity. In addition, the lens cover holder is removed and attached horizontally, decreasing the chance of the lens cover dropping into the surgical site during removal or attachment. The lens cover holder also attaches to the lens housing without telescoping, thus preserving the visual scope of the microscope.

Exemplary Alternate Embodiments

The following exemplary embodiments of the invention are not intended to represent each embodiment, or every aspect, of the present invention. The above features and advantages, and other features and advantages of the present invention, will become more readily apparent from the following description.

According to one embodiment of the present invention, a lens assembly for a medical drape is featured. The lens assembly comprises an annular lens housing that is attachable (e.g., via adhesives) to the medical drape. The lens housing is configured to engage with and thereby attach to the medical device. An annular lens cover holder is removably attachable to the lens housing. The lens assembly also includes a lens cover that is configured to shield the objective lens. The lens cover is hinged to the lens cover holder such that the lens cover is selectively pivotable with respect to the lens cover holder.

In accordance with one optional facet of the present invention, the lens cover holder has an internal chamber within which the lens cover pivots. Optionally, the internal chamber of the lens cover holder includes first and second angularly offset shoulders. Each shoulder presses against a respective portion of the lens cover to thereby restrict the pivot angle of the lens cover.

In accordance with another optional facet, the lens cover pivots about an axis that is generally transverse with respect to a longitudinal axis of the annular lens cover holder. It may be desirable that the lens cover be able to pivot at least 20 degrees. To that end, the lens cover may be provided with a tilt knob for selectively pivoting the lens cover.

As part of another optional facet of the present invention, the lens housing or the lens cover holder includes a flange that protrudes therefrom. Optionally, the flange extends around an outer perimeter of the annular lens housing or the annular lens cover holder. The other of the lens housing and the lens cover holder includes a complementary arcuate slot that receives the flange, thereby attaching the lens cover holder to the lens housing. Optionally, the arcuate slot extends over 180 degrees about an upper surface of the annular lens housing or annular lens cover holder. The flange may be fabricated from a flexible material such that the flange can be press-fit into engagement with the arcuate slot.

According to yet another aspect, the annular lens housing has an inner-diameter surface comprised of a flexible material. The flexible material allows the inner-diameter surface to frictionally engage with an outer-diameter surface of an objective lens housing and thereby attach the lens housing to the medical device. Additionally, or as an alternative thereto, the inner-diameter surface of the annular lens housing may be provided with a plurality of compliant protrusions that project inward therefrom. The protrusions engage with the outer-diameter surface of the objective lens housing to provide additional/alternative means for attaching the lens housing to the medical device.

As part of yet another aspect of the present invention, the lens housing and lens cover holder both have a common, fixed outer diameter, which eliminates the possibility of the lens cover holder and lens housing from telescoping with respect to one another. In contrast, the inner diameter of the lens housing may be selectively modifiable to accommodate objective lens housings of varying outer diameters. This optional configuration provides for a universal lens cover holder that is interchangeable with an array of lens housings that accommodate objective lens housings of varying sizes.

According to another embodiment of the present invention, a drape assembly is provided for creating a barrier between a sterile field and an optical device, such as a surgical microscope or camera. In this embodiment, the drape assembly includes a drape body comprising a flexible material sized to cover at least a portion of the optical device. A lens housing, which is attached to the drape body, is engageable with the optical device to attach thereto proximate to the objective lens of the optical device. The drape assembly also includes a lens cover holder that is removably attached to the lens housing to rotate about a first axis. A lens cover is mounted to the lens cover holder to pivot about a second axis that is different from the first axis.

In accordance with one optional facet of the present invention, the second axis is generally orthogonal with respect to the first axis.

As part of another optional aspect, a flange protrudes laterally from a bottom edge of the lens housing. In this instance, a complementary C-shaped slot projects upwardly from a top surface of the lens cover holder. The C-shaped slot is configured to receive the flange and thereby attach the lens cover holder to the lens housing. Ideally, the C-shaped slot extends over 180 degrees about the top surface of the lens cover holder.

According to another optional facet, the lens cover holder defines an internal chamber. The lens cover is positioned inside and spans across the internal chamber of the lens cover holder. The internal chamber of the lens cover holder may be provided with angularly offset shoulders, each of which is configured to obstruct the movement of the lens cover and thereby limit the pivoting range of the lens cover.

In accordance with yet another embodiment of the invention, a surgical drape assembly is presented for creating a barrier between a sterile field of an operating room and a surgical microscope. In this embodiment, the surgical drape assembly includes a drape body comprising a sheet-like material sized to cover substantially all of the surgical microscope. An annular lens housing is fixed to the drape body. The lens housing is configured to press-fit onto an annular objective lens housing of the surgical microscope, whereby the drape body is removably attached to the surgical microscope. An annular lens cover holder with an internal chamber is removably mounted to the lens housing to rotate about a first axis that is generally coaxial with a viewing axis of the microscope's objective lens. The surgical drape assembly also includes a substantially-transparent lens cover that is positioned inside and spans across the internal chamber of the lens cover holder. The lens cover is hinged to the lens cover holder to pivot about a second axis that is generally transverse with respect to the viewing axis of the objective lens.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A lens assembly for a drape adapted to cover at least a portion of an optical device having an objective lens, the lens assembly comprising:
   a lens cover configured to shield the objective lens;
   a lens cover holder attached to the lens cover; and
   a lens housing configured to attach to the drape, the lens housing being further configured to engage with and thereby attach to the optical device,
   wherein one of the lens housing and the lens cover holder includes a circular flange protruding therefrom, and the other of the lens housing and the lens cover holder includes a complementary C-shaped arcuate slot receiving therein the circular flange and thereby removably attaching the lens cover holder to the lens housing, the C-shaped arcuate slot extending over 180 degrees, but less than 360 degrees, along a perimeter of the other of the lens housing and the lens cover holder.

2. The lens assembly of claim 1, wherein the circular flange extends continuously around a perimeter of the one of the lens housing and the lens cover holder.

3. The lens assembly of claim 1, wherein the circular flange projects radially outward from the lens housing, and the C-shaped arcuate slot projects from the lens cover holder.

4. The lens assembly of claim 1, wherein the C-shaped arcuate slot extends over 200 degrees along the perimeter of the other of the lens housing and the lens cover holder.

5. The lens assembly of claim 1, wherein the circular flange is positioned inside the C-shaped arcuate slot by sliding the lens housing or the lens cover holder, or both, towards one another along a mutual lateral-plane in a shearing-type motion.

6. The lens assembly of claim 1, wherein the circular flange is fabricated from a rigid polymeric material and the C-shaped arcuate slot is fabricated from a flexible polymeric material such that the circular flange is press-fit into engagement with the C-shaped arcuate slot.

7. The lens assembly of claim 1, wherein the lens cover holder and the lens housing are both annular and concentrically aligned along a common longitudinal axis when attached.

8. The lens assembly of claim 1, wherein the lens cover holder defines an internal chamber, the lens cover being positioned inside and spanning across the internal chamber of the lens cover holder.

9. The lens assembly of claim 8, wherein the internal chamber of the lens cover holder includes opposing first and second semi-circular, wedge-shaped sections each of which receives therein a respective portion of the lens cover.

10. The lens assembly of claim 1, wherein the lens housing is annular and comprises an outer backing ring fabricated from a rigid polymer and an inner-diameter surface fabricated from a flexible polymer, the lens housing being configured to be pressed onto an objective lens housing of the optical device such that the inner-diameter surface of the lens housing compresses against and frictionally engages an outer surface of the objective lens housing.

11. A lens assembly of for a drape adapted to cover at least a portion of an optical device having an objective lens, the lens assembly comprising:
    a lens cover configured to shield the objective lens;
    a lens cover holder attached to the lens cover; and
    a lens housing configured to attach to the drape, the lens housing being further configured to engage with and thereby attach to the optical device,
    wherein one of the lens housing and the lens cover holder includes a circular flange protruding therefrom, and the other of the lens housing and the lens cover holder includes a complementary C-shaped arcuate slot receiving therein the circular flange and thereby removably attaching the lens cover holder to the lens housing,
    wherein positioning the circular flange inside the C-shaped arcuate slot allows the lens cover holder to rotate about a first axis, and
    wherein the lens cover is pivotably attached to the lens cover holder to pivot about a second axis extending generally transverse with respect to the first axis.

12. The lens assembly of claim 11, wherein the second axis of the lens cover is generally orthogonal with respect to the first axis of the lens cover holder.

13. A drape assembly for covering at least a portion of an optical device, the optical device having an objective lens housed in an objective lens housing, the drape assembly comprising:
- a flexible drape body sized to cover at least a portion of the optical device;
- a lens housing attached to the flexible drape body, the lens housing being configured to engage with the objective lens housing and thereby removably attach the drape assembly to the optical device;
- a lens cover holder defining an internal chamber; and
- a transparent or substantially transparent lens cover positioned inside and spanning across the internal chamber of the lens cover holder,
- wherein one of the lens housing and the lens cover holder includes a circular flange protruding therefrom, and the other of the lens housing and the lens cover holder includes a complementary C-shaped arcuate slot receiving therein the circular flange and thereby removably attaching the lens cover holder to the lens housing, the C-shaped arcuate slot extending over 180 degrees, but less than 360 degrees, along a perimeter of the other of the lens housing and the lens cover holder.

14. A method of assembling a drape assembly for covering an optical device having an objective lens, the method comprising:
- providing a transparent or substantially transparent lens cover configured to shield the objective lens;
- providing a lens cover holder;
- attaching the lens cover to the lens cover holder;
- providing a lens housing configured to engage with and thereby attach to the optical device proximate the objective lens;
- attaching the lens housing to a drape body; and
- attaching the lens cover holder to the lens housing, wherein one of the lens housing and the lens cover holder includes a circular flange protruding therefrom, and the other of the lens housing and the lens cover holder includes a complementary C-shaped arcuate slot receiving therein the circular flange and thereby attaching the lens cover holder to the lens housing, the C-shaped arcuate slot extending over 180 degrees, but less than 360 degrees, along a perimeter of the other of the lens housing and the lens cover holder.

15. The method of claim 14, wherein the circular flange extends continuously around a perimeter of the one of the lens housing and the lens cover holder.

16. The method of claim 14, wherein the circular flange projects radially outward from a bottom edge of the lens housing, and the C-shaped arcuate slot projects upwardly from the top surface of the lens cover holder.

17. The method of claim 14, wherein the C-shaped arcuate slot extends over 200 degrees along a perimeter of the other of the lens housing and the lens cover holder.

18. The method of claim 14, wherein the circular flange is positioned inside the C-shaped arcuate slot by sliding the lens housing or the lens cover holder, or both, towards one another along a mutual lateral-plane in a shearing-type motion.

19. The method of claim 14, wherein the circular flange is fabricated from a rigid polymeric material and the C-shaped arcuate slot is fabricated from a flexible polymeric material such that the circular flange is press-fit into engagement with the C-shaped arcuate slot.

20. A method of assembling a drape assembly for covering an optical device having an objective lens, the method comprising:
- providing a transparent or substantially transparent lens cover configured to shield the objective lens;
- providing a lens cover holder;
- attaching the lens cover to the lens cover holder;
- providing a lens housing configured to engage with and thereby attach to the optical device proximate the objective lens;
- attaching the lens housing to a drape body; and
- attaching the lens cover holder to the lens housing, wherein one of the lens housing and the lens cover holder includes a circular flange protruding therefrom, and the other of the lens housing and the lens cover holder includes a complementary C-shaped arcuate slot receiving therein the circular flange and thereby attaching the lens cover holder to the lens housing,
- wherein positioning the circular flange inside the C-shaped arcuate slot allows the lens cover holder to rotate about a first axis, and wherein the lens cover is pivotably attached to the lens cover holder to pivot about a second axis extending generally transverse with respect to the first axis.

* * * * *

UNITED STATES PATENT AND TRADEMARK OFFICE
CERTIFICATE OF CORRECTION

| | | |
|---|---|---|
| PATENT NO. | : 9,050,085 B2 | Page 1 of 1 |
| APPLICATION NO. | : 14/489752 | |
| DATED | : June 9, 2015 | |
| INVENTOR(S) | : Mark Spencer G. Chua | |

It is certified that error appears in the above-identified patent and that said Letters Patent is hereby corrected as shown below:

In the claims,

On Column 10, Line 45 (Claim 11, Line 1), delete "of" after "assembly"

Signed and Sealed this
Thirteenth Day of October, 2015

Michelle K. Lee
*Director of the United States Patent and Trademark Office*